United States Patent [19]

Cicco

[11] Patent Number: 5,026,924
[45] Date of Patent: Jun. 25, 1991

[54] PROCESS FOR PRODUCTION OF 1,2,2,2-TETRAFLUOROETHYL DIFLUOROMETHYL ETHER

[75] Inventor: Charles F. Cicco, Cleveland Heights, Ohio

[73] Assignee: Anaquest, Inc., Murray Hill, N.J.

[21] Appl. No.: 461,134

[22] Filed: Jan. 4, 1990

Related U.S. Application Data

[63] Continuation-in-part of Ser. No. 323,579, Mar. 14, 1989, abandoned.

[51] Int. Cl.$^5$ ............................................. C07C 41/22
[52] U.S. Cl. ..................................................... 568/683
[58] Field of Search ......................................... 568/683

[56] References Cited

U.S. PATENT DOCUMENTS

2,005,705  6/1935  Dandt et al. .
2,005,708  6/1935  Dandt et al. .
3,535,388  10/1970 Terrell .
3,869,519  3/1975  Terrell .
3,962,460  6/1976  Croix et al. .

FOREIGN PATENT DOCUMENTS

129863  1/1985  European Pat. Off. .
2361058  6/1975  Fed. Rep. of Germany .

*Primary Examiner*—Howard T. Mars
*Attorney, Agent, or Firm*—R. Hain Swope; Larry R. Cassett

[57] ABSTRACT

A process is provided for the low temperature preparation of $CF_3CHFOCHF_2$ which comprises reacting $CF_3CHClOCHF_2$ with hydrogen fluoride in the presence of an antimony pentachloride catalyst or mixture of antimony pentachloride and antimony trichloride.

19 Claims, No Drawings

PROCESS FOR PRODUCTION OF 1,2,2,2-TETRAFLUOROETHYL DIFLUOROMETHYL ETHER

RELATED APPLICATIONS

This application is a continuation-in-part of U.S. Pat. application Ser. No. 07/323,579, filed Mar. 14, 1989, now abandoned.

FIELD OF THE INVENTION

The present invention is directed to the field of inhalation anesthetics. More specifically, this invention is directed to a novel, low temperature process for the preparation of 1,2,2,2-tetrafluoroethyl difluoromethyl ether.

BACKGROUND OF THE INVENTION

The compound 1,2.2,2-tetrafluoromethyl difuoroethyl ether ($CF_3CHFOCHF_2$) is an important volatile liquid inhalation anesthetic particularly suited for administration to patients during outpatient surgery due to its rapid rate of recovery. Economical methods for the preparation of $CF_3CHFOCHF_2$ using inexpensive, available raw materials are therefore highly desirable.

One known method for preparing $CF_3CHFOCHF_2$ is by first chlorinating 1,2,2,2-tetrafluoroethyl methyl ether ($CF_3CHFOCH_3$) to produce a compound having the formula $CF_3CHFOCHCl_2$, which compound is then fluorinated with hydrogen fluoride in the presence of antimony pentachloride. See, for example, Ger. Offen. 2,361,058 (1975). However, such a process is disadvantageous for producing $CF_3CHFOCHF_2$ on an industrial scale as it is a complex, multiple-step synthesis which can require large amounts of chlorine and is, therefore, both cumbersome and expensive.

The use of hydrogen fluoride with antimony pentachloride as a catalyst as in the above process is nevertheless an attractive method of preparing fluorinated hydrocarbon derivatives such as the subject compound as such well known technology has been used in industry for years and involves inexpensive, readily available raw materials.

U.S. Pat. No. 2,005,708, for example, describes the production of chlorofluoroalkanes from the reaction of a chlorinated hydrocarbon with hydrogen fluoride in the presence of an antimony halide, for example, antimony pentachloride or a mixture of antimony pentachloride and antimony trichloride. U.S. Pat. No. 2,005,705 also describes fluorination of organo chlorine compounds, for example, carbon tetrachloride, methylene chloride, fluorotrichloro methane and the like, with hydrogen fluoride in the presence of an antimony pentachloride catalyst to produce chlorofluoro alkanes. Further, European Application No. 129,863 describes a process whereby antimony pentachloride is first reacted with hydrogen fluoride to produce an antimony chlorofluoride, which is then reacted with a haloalkane, for example, carbon tetrachloride, penta- and hexachloroethane and the like. to produce mixtures of fluoro and chlorofluoroalkanes. None of these references teaches or suggests a means of replacing chloro with fluoro on an internal carbon atom in a chlorofluoro ether containing at least three carbon atoms.

The processes described above, however, have not contemplated the preparation of fluorinated organoethers such as $CF_3CHFOCHF_2$. Moreover, the formation of highly fluorinated hydrocarbons by such processes typically involve relatively high reaction temperatures and pressures which, in addition to incurring high energy costs, can cause decomposition of reactants and products and rapid deterioration of process materials.

It is, therefore, an object of this invention to provide an economical, energy efficient process employing mild reaction conditions for the preparation of $CF_3CHFOCHF_2$ using inexpensive, readily available raw materials.

SUMMARY OF THE INVENTION

The present invention provides a novel low temperature process for the preparation of 1,2,2,2-tetrafluoroethyl difluoromethyl ether ($CF_3CHFOCHF_2$) which comprises reacting isoflurane ($CF_3CHClOCHF_2$) with hydrogen fluoride in the presence of substantially pure antimony pentachloride catalyst or a catalyst containing a major portion of antimony pentachloride and a minor portion of antimony trichloride.

DETAILED DESCRIPTION OF THE INVENTION

In the process of the present invention, the starting compound, isoflurane ($CF_3CHClOCHF_2$), is contacted with a source of hydrogen fluoride in the presence of at least one antimony chloride catalyst to replace the single chlorine atom in isoflurane with a fluorine atom at conditions of relatively low temperature in the range of between about $-10°$ C. to $30°$ C., preferably about $-7°$ C. to $18°$ C. The pressure of the reaction can vary, but is generally in the range of from about 12 to 70 psia, preferably from about 15 to 22 psia.

The compound isoflurane can be obtained from methods known in the art including those disclosed in U.S. Pat. No. 3,535,388, which is incorporated herein by reference. The choice of isoflurane as a starting material is particularly critical since, in the subject reaction, it does not produce a mixture of isomers which require expensive distillation/separation techniques. Reactions which produce such mixtures are not suited for cost-efficient production on a large scale.

The type of hydrogen fluoride used to fluorinate isoflurane in the presence of the antimony chloride catalyst is preferably a commercial grade of hydrogen fluoride i.e. a pure product or a product containing only small amounts of impurities. The presence of water in the reaction is not desirable and, thus, it is preferred to use substantially anhydrous hydrogen fluoride. For convenience and ease of preparation, it is preferable to use gaseous hydrogen fluoride although liquid hydrogen fluoride may be used as well.

The antimony chloride useful herein is preferably substantially pure antimony pentachloride, available in commercial grade purities of 99% purity or more. Also useful herein are mixtures containing a major portion of antimony pentachloride and a minor portion of antimony trichloride. Antimony pentachloride or mixtures thereof is preferably used in anhydrous form, but can also be used as a solution, for example, in dichloromethane.

Those skilled in the art are aware that hydrogen fluoride and antimony chloride, e.g. antimony pentachloride, react to form a mixed antimony fluorochloride catalyst in situ. Such a mixed catalyst would be likewise useable in the present invention and is contemplated herein. However, the present process is preferenced in economy. For reasons of economy, it is preferred to utilize pure antimony chloride and form the mixed catalyst in situ.

As described hereinabove, the fluorination of isoflurane with hydrogen fluoride in the presence of the antimony pentachoride catalyst can be carried out at relatively low temperatures in the range of from about −10° C. to about 30° C., preferably in the range of from about −7° C. to about 18° C.

The molar ratio of isoflurane to hydrogen fluoride in the reaction mixture can vary, but is generally from about 1:0.1 to about 1:7, preferably from about 1:1 to about 1:4, and most preferably about 1:2.

Depending on the molar ratio of reactants employed, a catalytically effective amount of substantially pure antimony pentachloride or a mixture of antimony pentachloride with minor amounts of antimony trichloride is employed. Such amounts can easily be determined without undue experimentation, but are preferably from about 1.0 to about 6.0 weight percent based on the total weight of the reaction mixture.

In a preferred embodiment of this invention, a pressure reaction vessel having a gas inlet, for example, a Parr pressure reactor, is charged with isoflurane and an effective amount of the antimony chloride catalyst. The reaction vessel is also preferably fitted with a cooling bath. Hydrogen fluoride can be conveniently introduced to the reaction mixture by fitting a gas cylinder filled with hydrogen fluoride gas to the inlet of the pressure reaction vessel. Through the use of a valve, the flow rate of the gas to the reaction mixture can easily be regulated. If desired, the conduit connecting the gas cylinder to the reaction vessel can be submerged, for example, in a mineral oil bath and the like to maintain an effective temperature whereby the effluent cylinder pressure is higher than the pressure in the reaction mixture to insure a steady flow of gas to the reaction mixture by pressure differential. The rate of addition of hydrogen fluoride gas to the reaction mixture is not critical to the process of this invention, and can vary widely. However, experience has shown that the gas is preferably added at the rate of about 0.01 to about 0.1 parts by weight per hour. The pressure in the reaction vessel may be in the range of from about 12 psia to about 70 psia, preferably from about 15 psia to about 22 psia. The reaction vessel is preferably supplied with a mixer or agitator to insure maximum contact between the reactants during the fluorination reaction.

Hydrogen chloride gas which is given off as the fluorination reaction progresses can be passed to a scrubbing vessel to be absorbed, for example, in an aqueous caustic soda solution. The final reaction mixture can then be neutralized with water and caustic soda, and the organic phase separated by fractional distillation to produce the desired product $CF_3CHFOCHF_2$ and unreacted starting material $CF_3CHClOCHF_2$.

Other characteristics and descriptions of $CF_3CHFOCHF_2$ and anesthetic compositions containing the compound are disclosed in Terrell, U.S. Pat. No. 4,762,856, incorporated herein by reference.

The following examples will serve to more fully illustrate the practice of preferred embodiments of the present invention. Such examples are intended to be for illustrative purposes only and are not intended to limit the scope of this invention.

EXAMPLE 1

The following example illustrates a preferred embodiment of the process of the present invention for the production of $CF_3CHFOCHF_2$ from $CF_3CHClOCHF_2$ utilizing a molar ratio of isoflurane to hydrogen fluoride of about 1:2.

Isoflurane ($CF_3CHClOCHF_2$) (166.4 kilograms, 0.902 kilogram mole) was added to a 50 gallon stainless steel reaction vessel fitted with an agitator. Antimony pentachloride (4.76 kilograms) was then added and the contents of the vessel cooled to 14° C. Liquid anhydrous hydrogen fluoride was added next to the stirred contents of the vessel at a rate of about 4.3 kilograms per hour for a total of eight hours. The total hydrogen fluoride added was 34.5 kilograms (1.725 kilogram-moles). The reaction was allowed to continue without further hydrogen fluoride addition at 10°–14° C. for two additional hours, after which gas chromatographic analysis of the reaction mixture showed 73% conversion of $CF_3CHClOCHF_2$ to the desired product, $CF_3CHFOCHF_2$. After sampling, the reaction was allowed to continue for an additional two hours. The reaction pressure during the entire reaction period was maintained in the range of 1–7 psig.

The reaction mixture was then chilled to about 2° C. by cooling with recirculating ethylene glycol solution, then transferred to a 200 gallon plastic tank containing 70 gallons of water. The organic phase was recirculated through the water, then transferred to another 200 gallon tank containing 15 gallons of 50% sodium hydroxide solution and 70 gallons of water. The organic phase was then recirculated through the alkaline solution to remove excess acidity and permitted to settle after which the organic layer was transferred to a drum. Additional crude organic product, $CF_3CHFOCHF_2$, was obtained from a post scrubber condenser.

$CF_3CHFOCHF_2$ is normally a clear, colorless liquid having the following physical properties: boiling point 23.5° C., molecular weight 168, estimated vapor pressure 660 mmHg, at 20° C., and a specific gravity of 1.44. IR shows a prominent peak at 4903 $CM^{-1}$ and 'H NMR shows a triplet at 6.5 ppm (J=70 Hz) and a doublet of quartets at 5.9 ppm ($J_{gem}$=56 Hz, $J_{vic}$=3 Hz). The compound is noninflammable and stable to soda lime rendering it particularly suitable for use as an inhalation anesthetic.

A total of 141.9 kilograms of crude reaction product was obtained containing 80.7% $CF_3CHFOCHF_2$ and 15.8% $CF_3CHClOCHF_2$, as determined by gas chromatography. The conversion of isoflurane was 78.2% according to the calculation $$\text{Percent conversion} = \frac{\text{moles of product obtained}}{\text{moles of isoflurane in}} \times 100$$

Eight additional runs under essentially similar reaction conditions produced an overall average conversion of 74.5%.

The percentage recovery of starting material plus product was 92.3% according to the calculation $$\text{Percent Recovery} = \frac{\text{moles of isoflurane + product obtained}}{\text{moles of isoflurane in}} \times 100$$

Eight additional runs under essentially similar reaction conditions produced an overall average recovery of 90.7%.

The percentage yield of product was 90.9% to the calculation $$\text{Percent yield} = \frac{\text{moles of product obtained}}{\text{moles of isoflurane consumed}} \times 100$$

Eight additional runs under essentially similar conditions reaction produced an overall average yield of 88.9%.

EXAMPLE 2

Using a procedure similar to Example 1, isoflurane (170.1 Kg. 0.92 kilogram mole) and hydrogen fluoride (71 Kg. 3.6 Kilogram mole) were reacted in the presence of 5.1 Kg. of antimony pentachloride. The molar ratio of isoflurane to HF was about 1:4. The crude product isolated (143.3 Kg.) contained 27.8% $CF_3CHFOCHF_2$ and 71.8% isoflurane. The yield was 65.1%, the conversion 25.7%, and the recovery 86.2%.

EXAMPLE 3

Using a procedure similar to Example 1, isoflurane (170.5 Kg. 0.92 kilogram mole), hydrogen fluoride (92 Kg. 4.6 kilogram mole) and antimony pentachloride (5.12 Kg.) were combined in a reactor. The molar ratio of isoflurane to HF was about 1:5. An additional 2.33 Kg. of antimony pentachloride was added to the reactor after 10 hours. The crude product (137.9 Kg) contained 36.6% $CF_3CHFOCHF_2$ and 62.8% isoflurane for a yield of 65.9%, conversion of 32.5% and recovery of 83.2%.

EXAMPLE 4

Isoflurane (55.2 Kg. 0.3 kilogram mole), hydrogen fluoride (41.3 Kg. 2.1 kilogram mole) and antimony pentachloride (5.2 Kg.) were utilized in a similar manner to prepare 42.1 Kg. of crude product containing 57.6% $CF_3CHFOCHF_2$ and 42.% isoflurane. The yield was 70.9%, the conversion 48.2%, and the recovery 80.2%. The molar ratio of isoflurane to HF was about 1:7.

EXAMPLE 5

Isoflurane (83.2 g. 0.45 mole). hydrogen fluoride (9.4 g. 0.47 mole), and antimony pentachloride (2.4 g.) were used to prepare 72.2 g. of crude product containing 18.8% $CF_3CHFOCHF_2$ and 81.2% isoflurane. The molar ratio of isoflurane to HF was about 1:1. The yield was 60.9%, conversion 18.0%. and the recovery 83.5%.

EXAMPLE 6

Isoflurane (83.2 g. 0.45 mole), hydrogen fluoride (4.4 g. 0.22 mole), and antimony pentachloride (2.4 g.) were used to prepare 68.6 g. of crude product containing 16.8% $CF_3CHFOCHF_2$ and 83.2% isoflurane. The molar ratio of isoflurane to HF was about 1:0.5. The yield was 47.7%, conversion 15.0%, and the recovery 78.6%.

EXAMPLE 7

Isoflurane (83.2 g. 0.45 mole), hydrogen fluoride (1.2 g. 0.06 mole), and antimony pentachloride (2.4 g.) were used to prepare 72.6 g. of crude product containing 6.1% $CF_3CHFOCHF_2$ and 93.9% isoflurane. The molar ratio of isoflurane to HF was about 1:0.13. The yield was 32.1%, conversion 5.8% and the recovery 87.84%.

I claim:

1. A process for the preparation of a compound of the formula $CF_3CHFOCHF_2$ comprising reacting a starting compound of the formula $CF_3CHClOCHF_2$ with hydrogen fluoride and a catalytically effective amount of substantially pure antimony pentachloride or antimony pentachloride in combination with antimony trichloride at a temperature of from about $-10°$ C. to about $30°$ C. wherein the ratio of $CF_3CHClOCHF_2$ to hydrogen fluoride is from about 1.0:0.1 to about 1:7.

2. A process in accordance with claim 1 wherein the catalyst is substantially pure antimony pentachloride.

3. A process in accordance with claim 1, wherein the reaction is conducted at a temperature in the range of about $-7°$ C. to about $18°$ C.

4. A process in accordance with claim 1, wherein $CF_3CHClOCHF_2$ is combined with said catalytically effective amount of antimony pentachloride and the resulting mixture is contacted with hydrogen fluoride to produce $CF_3CHFOCHF_2$.

5. A process in accordance with claim 1, wherein the molar ratio of $CF_3CHClOCHF_2$ to hydrogen fluoride is from about 1:1 to about 1:4.

6. A process in accordance with claim 5, wherein the molar ratio of $CF_3CHClOCHF_2$ to hydrogen fluoride is about 1.2.

7. A process in accordance with claim 1, wherein the catalytically effective amount of the catalyst is from about 1.0 to 6.0 weight percent, based on the total weight of the reaction mixture.

8. A process in accordance with claim 1. wherein the catalyst is substantially anhydrous.

9. A process in accordance with claim 3, wherein the hydrogen fluoride is supplied as a gas at the rate of about 0.01 to about 0.1 parts by weight per hour.

10. A process in accordance with claim 1, wherein the hydrogen fluoride is substantially anhydrous.

11. A process in accordance with claim 1, wherein the reaction is carried out at a pressure of from about 12 to 70 psia.

12. A process in accordance with claim 11, wherein the reaction is carried out at a pressure of from about 15 to 22 psia.

13. A process for the preparation of a compound of the formula $CF_3CHFOCHF_2$ comprising reacting a starting compound having the formula $CF_3CHClOCHF_2$ with substantially anhydrous hydrogen fluoride wherein the molar ratio of $CF_3CHClOCHF_2$ to hydrogen fluoride is in the range of from about 1:0.1 to about 1:7, and substantially anhydrous and substantially pure antimony pentachloride or a mixture of antimony pentachloride and antimony tricholoride in a catalytically effective amount of from about 1.0 to 6.0 weight percent based on the total weight of the reaction mixture, at a temperature of from about $-10°$ C. to about $30°$ C.

14. A process in accordance with claim 13, wherein hydrogen fluoride is supplied as a gas at the rate of about 0.01 to about 0.1 parts by weight per hour.

15. A process in accordance with claim 13. wherein the molar ratio of $CF_3CHClOCHF_2$ to hydrogen fluoride is from about 1:1 to about 1.4.

16. A process in accordance with claim 15, wherein the molar ratio of $CF_3CHClOCHF_2$ to hydrogen fluoride is about 1:2.

17. A process in accordance with claim 13, wherein the catalyst is substantially pure antimony pentachloride.

18. A process in accordance with claim 13, wherein the reaction is carried out at a pressure of from about 12 to 70 psia.

19. A process in accordance with claim 18, wherein the reaction is carried out at a pressure of from about 15 to 22 psia.

* * * * *